(12) United States Patent
Sugai et al.

(10) Patent No.: US 8,852,584 B2
(45) Date of Patent: Oct. 7, 2014

(54) BACTERICIDE HAVING SELECTIVITY TO CARIOGENIC BACTERIUM, AND A METHOD FOR STERILIZATION OF CARIOGENIC BACTERIUM

(75) Inventors: Motoyuki Sugai, Hiroshima (JP); Hitoshi Komatsuzawa, Hiroshima (JP)

(73) Assignee: Two Cells Co., Ltd., Hiroshima (JP)

( * ) Notice: Subject to any disclaimer, the term of this patent is extended or adjusted under 35 U.S.C. 154(b) by 1246 days.

(21) Appl. No.: 11/921,876

(22) PCT Filed: Jul. 25, 2006

(86) PCT No.: PCT/JP2006/314671
§ 371 (c)(1),
(2), (4) Date: Dec. 21, 2007

(87) PCT Pub. No.: WO2007/013452
PCT Pub. Date: Feb. 1, 2007

(65) Prior Publication Data
US 2009/0274635 A1    Nov. 5, 2009

(30) Foreign Application Priority Data

Jul. 26, 2005   (JP) .................... 2005-216099
Jul. 20, 2006   (JP) .................... 2006-198407

(51) Int. Cl.
| | |
|---|---|
| A61K 38/47 | (2006.01) |
| C12N 9/26 | (2006.01) |
| C12N 1/00 | (2006.01) |
| C12N 1/20 | (2006.01) |
| C12N 9/36 | (2006.01) |
| A61Q 11/00 | (2006.01) |
| A61K 8/37 | (2006.01) |
| C12N 9/24 | (2006.01) |
| A61K 8/66 | (2006.01) |
| C12N 9/00 | (2006.01) |

(52) U.S. Cl.
CPC .............. *A61Q 11/00* (2013.01); *C12N 9/2462* (2013.01); *A61K 38/47* (2013.01); *A61K 8/375* (2013.01); *C12N 9/2402* (2013.01); *A61K 8/66* (2013.01); *C12N 9/00* (2013.01)
USPC ........ 424/94.6; 435/201; 435/243; 435/253.4

(58) Field of Classification Search
CPC ..... A61Q 11/00; C12N 9/2402; C12N 9/2406
See application file for complete search history.

(56) References Cited

U.S. PATENT DOCUMENTS 4,725,428 A * 2/1988 Miyahara et al. ............ 424/50
7,776,325 B2 * 8/2010 Sugai et al. ............... 424/94.1

FOREIGN PATENT DOCUMENTS

| | | | |
|---|---|---|---|
| AU | 2004298951 B2 | 6/2005 | |
| EP | 1 716 862 A1 | 11/2006 | |
| JP | 52-96750 | * | 8/1977 |
| JP | 55-102511 | * | 8/1980 |
| JP | A 59-71688 | 4/1984 | |
| JP | A 2-83336 | 3/1990 | |
| JP | A 7-196463 | 8/1995 | |
| JP | A 9-322763 | 12/1997 | |
| JP | A-2000-159675 | 6/2000 | |
| JP | 3178888 | * | 4/2001 |
| JP | A 2005-179205 | 7/2005 | |
| WO | WO 92/05766 | 4/1992 | |
| WO | WO 2005/058343 A1 | * | 6/2005 |

OTHER PUBLICATIONS

Yoshimura et al. Jun. 2004, Zymographic characterization of bacteriolytic enzymes produced by oral *Streptococci*. Microbiology and Immunology, vol. 48(6), pp. 465-469.*
Translation of JP 52-96750 abstract.*
Translation of JP 55-102511 abstract.*
Wang. CRC Press LLC. 3 Saccharides: Modifications and Applications. 2004.*
Shibata et al. Identification and characterization of an autolysin-encoding gene of *Streptococcus mutans*. Infect. Immun. 73:3512-3520. Jun. 2005.*
Branden et al. Introduction to Protein Structure, Garland Publishing Inc., New York, p. 247, 1991.*
Ash et al. Handbook of Green Chemicals, Synapse Information Resources, Inc, 2004, pp. 1042 and 1044.*
Machine Translation of JP 3178888—retrieved from JST on Mar. 6, 2014.*
Yukie Shibata et al., "Identification and Characterization of an Autolysin-Encoding Gene of *Streptococcus mutans*," Infection and Immunity, vol. 73, No. 6, pp. 3512-3520, Jun. 2005.
S.E. Coleman et al., "Lysis of Grouped and Ungrouped *Streptocci* by Lysozyme," Infection and Immunity, vol. 2, No. 5, pp. 563-569, Nov. 1970.
L. V. Thomas et al., "Synergist Effect of Sucrose Fatty Acid Esters on Nisin Inhibition of Gram-Positive Bacteria," Journal of Applied Microbiology, vol. 85, pp. 1013-1022, 1998.
Bruce M. Chassy et al., Method for Lysis of Gram-Positive, Asporogenous Bacteria With Lysozyme, Applied and Environmental , vol. 39, No. 1, pp. 153-158, Jan. 1980.
Shigeyuki Hamada, Characterization of Virulence Factors of Mutans *Streptococci* and Specific Inhibition of These Factors, Japanese Journal of Bacteriology, vol. 51, No. 4, pp. 931-951, 1996 (with partial English-language Translation).
Yuko Tomita et al., "P1-211 Cell Wall Digesting Enzyme: Aml Lyses *S. mutans* and *S. sobrinus* Specifically," Japanese Journal of Bacteriology, vol. 60, No. 1, pp. 115, 2005 (with English-language Translation).
Feb. 4, 2011 Office Action in related Australian Application No. 2006273330.
Aug. 7, 2012 Office Action issued in Japanese Patent Application No. 2007-528475 (with translation).
Oct. 25, 2011 Office Action issued in Japanese Application No. JP 2007-528475 (with Translation).
Apr. 3, 2012 Office Action issued in Japanese Patent Application No. 2007-528475 (with English-language translation).

* cited by examiner

*Primary Examiner* — Yong Pak
(74) *Attorney, Agent, or Firm* — Oliff PLC

(57) ABSTRACT

The bacteriolytic effect of a bacterial cell wall lytic enzyme can be increased by the addition of a surfactant to the enzyme. As a result, the time required for lysis of cariogenic bacterium with the bacterial cell wall lytic enzyme can be shortened, and the practical utility of the bacterial cell wall lytic enzyme (such as automutanolysin) as a prophylactic or therapeutic agent for dental caries can be improved.

4 Claims, 4 Drawing Sheets

SEQUENCE LISTING

<160> NUMBER OF SEQ ID NOS: 2

<210> SEQ ID NO 1
<211> LENGTH: 979
<212> TYPE: PRT
<213> ORGANISM: Streptococcus mutans

<400> SEQUENCE: 1

Met Lys Ser Lys Thr Tyr Leu Met Ile Pro Leu Ala Leu Thr Leu Phe
1               5                   10                  15

Met Ala Ala Asn Lys Ile Ser Ala Asp Glu Gln Asn Gln Ser Leu Ser

```
            20                  25                  30
Ala Ser Glu Val Ile Ser Ser Asp Ala Thr Ser Val Ser Glu Leu Pro
            35                  40                  45

Ala Thr Thr Ala Gln Ile Ser Gln Glu Val Arg Asn Asn Gly Gln Asp
 50                  55                  60

Ser Thr Ile Gln Leu Gln Gln Thr Gln Glu Gln Ser Asp Pro Ile Thr
 65              70                  75                  80

Ser Thr Ser Glu Thr Thr Val Ser Ser Met Lys Ala Ala Thr Asn Gly
                    85                  90                  95

Ser Pro Ala Lys Ala Asn Glu Thr Glu Thr Val Pro Ser Gln Ala Ser
                100                 105                 110

Thr Ala Ser Ser Val Gln Thr Pro Asp Gln Ile Leu Thr Val Pro Ser
            115                 120                 125

Val Lys Ala Glu Thr Thr Ser Thr Ala Asp Gln Leu Gln Ser Thr Ser
            130                 135                 140

Ser Ala Pro Leu Asp Gln Gln Thr Asp Ala Lys Arg Leu Ser Asn Lys
145                 150                 155                 160

Met Thr Pro Ala Ser Ser Val Gln Ala Arg Ser Ser Leu Thr Gln Asp
                165                 170                 175

Lys Gln Val Gln Ala Gln Glu Val Thr Ser Ala Val Val Glu Glu Lys
                180                 185                 190

Gly Ile Lys Leu Gln Tyr Asn Gly Gln Ile Ala Arg Asn Thr Lys Ile
                195                 200                 205

Gln Phe Ala Val Trp Ser Ala Arg Asn Asp Gln Asp Asp Leu Gln Trp
                210                 215                 220

Tyr Thr Ala Asn Asn Met Gly Ala Ala Tyr Ala Glu Phe Lys Asn His
225                 230                 235                 240

Arg Glu Tyr Gly Thr Tyr Val His Thr Tyr Ala Asn Gln Asn Gly
                245                 250                 255

Lys Met Ile Gly Leu Asn Ala Thr Thr Leu Thr Ile Ala Gln Pro Gln
                260                 265                 270

Val Gln Thr Asn Ile Gln Arg Lys Ser Ala Thr Asn Phe Glu Leu Thr
            275                 280                 285

Val Ser Asn Val Pro Asn Thr Ile Ser Gly Ile Met Val Pro Val Trp
            290                 295                 300

Ser Asp Gln Asn Gly Gln Asp Ile Lys Trp Tyr Asn Ala Arg Lys
305                 310                 315                 320

Ala Asp Asp Gly Ser Tyr Lys Val Leu Ile Asp Thr Lys Asn His Lys
                325                 330                 335

Asn Asp Leu Gly His Tyr Glu Ala His Ile Tyr Gly Tyr Ser Thr Val
                340                 345                 350

Thr Gln Ser Gln Ile Gly Leu Ala Val Ser Ser Gly Phe Asp Arg Asn
            355                 360                 365

Asp Thr Arg Pro Asn Ala Arg Ile Ser Val Ala Asn Tyr Asp Gln Asn
            370                 375                 380

Lys Thr Thr Phe Asp Val Val Glu Gly Ser Ser Asp Thr Lys Thr
385                 390                 395                 400

Val Ser Ala Val Asn Ile Ala Val Trp Ser Glu Asp Lys Gly Gln Asp
                405                 410                 415

Asp Leu Lys Trp Tyr Ser Pro Lys Ile Val Asp Asn Lys Ala Thr Val
                420                 425                 430

Thr Ile Asn Ile Ala Asn His Ser Asn Thr Ser Asp Lys Tyr Asn Val
            435                 440                 445
```

```
His Val Tyr Thr Asp Tyr Thr Asp Gly Thr His Ser Gly Thr Ile Leu
    450                 455                 460

Gly Ala Tyr Gln Ile Asn Lys Pro Leu Glu Lys Asn Thr Val Ser Ala
465                 470                 475                 480

Asp Leu Thr Ser Asp Gly Ile Ala Leu Lys Leu Asp Ser Asn Thr Val
                485                 490                 495

Thr Asp Tyr Thr Lys Val Arg Phe Ala Val Trp Ser Asp Gln Asn Gly
            500                 505                 510

Gln Asp Asp Leu Lys Trp Tyr Ser Ala Asn Ser Asp Gly Thr Ala Thr
        515                 520                 525

Ala Ala Tyr Ser Asn His Ser Gly Tyr Gly Leu Tyr His Ile His Thr
    530                 535                 540

Tyr Ile Ile Lys Asp Gly Lys Met Val Gly Leu Asn Gly Lys Thr Ile
545                 550                 555                 560

Thr Ile Asn Gln Pro Ser Ala Lys Val Asp Ile Ala Lys Glu Ser Asp
                565                 570                 575

Ala Leu Tyr Lys Val Thr Val Ser Asn Leu Pro Ala Tyr Ile Ser Ser
            580                 585                 590

Val Val Ile Pro Val Trp Thr Asp Lys Asn Asn Gln Asp Asp Ile Gln
        595                 600                 605

Trp Ile Pro Ala Thr Lys Gln Gly Asp Gly Thr Tyr Ala Ala Gln Ile
    610                 615                 620

Gln Leu Ala Asp His Asn Gly Glu Thr Gly His Tyr Asn Val His Val
625                 630                 635                 640

Tyr Gly Gln Ser Lys Phe Asp Asn Lys Ala Val Gly Leu Ala Ala Thr
                645                 650                 655

Asp Gly Phe Asn Val Ala Glu Thr Arg Asn Ala Val Ile Ala Ala Ser
            660                 665                 670

Asn Tyr Asn Ala Ser Ala Gly Thr Ile Asp Met Ile Val Lys Gln Glu
        675                 680                 685

Ala Gly Gly Lys Ala Ile Lys Glu Val Arg Ile Ala Ala Trp Ser Glu
    690                 695                 700

Ala Asp Gln Ser Asn Leu His Trp Tyr Val Ser Ser Thr Ile Ile Asp
705                 710                 715                 720

Gly Lys Val Thr Val Thr Ile Asn Glu Lys Asn His Gln Tyr Ile Lys
                725                 730                 735

Gly Asn Tyr Asn Ile His Val Tyr Val Asp Tyr Thr Asp Gly Thr Ser
            740                 745                 750

Ser Gly Thr Asn Ile Gly Asn Tyr Ser Leu Asn Ala Asp Lys Pro Ala
        755                 760                 765

Val Ala Leu Pro Ser Tyr Phe Ile Asp Ile Ser Ser His Asn Gly Ile
    770                 775                 780

Ile Ser Val Ala Glu Phe Asn Ser Leu Lys Gln Gln Gly Ile Gln Gly
785                 790                 795                 800

Val Val Val Lys Leu Thr Glu Gly Thr Ser Tyr Ile Asn Pro Tyr Ala
                805                 810                 815

Ser Ser Gln Ile Ala Asn Ala Arg Ala Ala Gly Ile Lys Val Ser Ala
            820                 825                 830

Tyr His Tyr Ala His Tyr Thr Ser Ala Ala Gly Ala Gln Glu Glu Ala
        835                 840                 845

Arg Tyr Phe Ala Asn Ala Ala Arg Ser Phe Gly Leu Glu Ala Ser Thr
    850                 855                 860
```

-continued

Val Met Val Asn Asp Met Glu Glu Ser Ser Met Val Asn Asn Ile Asn
865                 870                 875                 880

Asn Asn Val Gln Ala Trp Gln Asp Glu Met Arg Arg Gln Gly Tyr Ser
            885                 890                 895

Asn Leu Ile His Tyr Thr Met Ala Ser Trp Leu Asp Ile Arg Gly Gly
            900                 905                 910

Gln Val Asp Thr Ala Arg Phe Gly Ile Asn Asn Phe Trp Val Ala His
            915                 920                 925

Tyr Ala Lys Gly Tyr Thr Tyr Met Thr Gln Glu Ala Lys Ser Leu
    930                 935                 940

Asn Tyr Tyr Ala Asn Ala Ala Ala Trp Gln Tyr Thr Ser Val Ser Ser
945                 950                 955                 960

Lys Leu Ser His Ala Leu Asp Glu Asn Ile Asp Tyr Thr Gly Arg Phe
            965                 970                 975

Thr Gln Gln

<210> SEQ ID NO 2
<211> LENGTH: 2940
<212> TYPE: DNA
<213> ORGANISM: Streptococcus mutans

<400> SEQUENCE: 2

| | |
|---|---|
| atgaaaagca aaacttattt gatgattcca ttagcattga ccctatttat ggctgctaat | 60 |
| aaaatatctg cagatgagca aaatcaatcc ttaagtgcat cagaagttat ttcttctgat | 120 |
| gcgacatcag tatctgaatt accagcgaca acagcacaga taagtcagga ggtcagaaat | 180 |
| aatggacaag acagtactat tcaattgcag caaacacagg aacagtctga tccgataaca | 240 |
| agtacgtctg agacaactgt ttcctctatg aaggcggcca caaatggctc acctgccaaa | 300 |
| gcaaatgaga ctgaaacagt tccgtctcag gcaagtactg ctagttctgt gcagactcct | 360 |
| gatcagattt tgactgttcc ctctgtaaaa gcggaaacca cttctaccgc agatcaatta | 420 |
| caatcaacat cgtctgctcc tttggatcaa caaactgatg ctaaacgtct ttccaataaa | 480 |
| atgaccccag caagcagcgt acaagctcgt tcttctctta cacaagacaa gcaagtacag | 540 |
| gcacaagaag tcacaagtgc tgtagtggaa gaaaaaggga ttaagctaca gtataacggt | 600 |
| cagatcgctc gaaatactaa gattcaattt gctgtctggt cagctcgaaa tgatcaagat | 660 |
| gatcttcaat ggtatacggc aaataatatg ggagcggcct atgccgaatt caagaatcat | 720 |
| cgagagtatg ggacctatta tgttcatact tatgctaatc aaaatggcaa gatgatagga | 780 |
| cttaacgcaa caactcttac aattgctcaa cctcaggtgc aaactaatat tcaaagaaaa | 840 |
| tcagcaacga ttttgagtt aaccgtttct aatgttccta atactattag cggcatcatg | 900 |
| gtacctgtct ggtcagatca aaacggtcaa gatgatatta atggtataaa tgcccgaaag | 960 |
| gctgatgatg gcagttataa ggttttgatt gatactaaaa atcacaagaa tgatttggga | 1020 |
| cattatgaag ctcatatttta cggctacagc acagtaaccc agtctcaaat ggcttagct | 1080 |
| gttagttctg gttttgaccg caatgatact agacccaatg caaggatatc tgttgctaat | 1140 |
| tatgaccaaa ataaaacgac ctttgatgtt gttgttgagg ttcatctga tacaaagact | 1200 |
| gtatctgctg ttaatattgc tgtttggtct gaagataaag gtcaagatga ccttaagtgg | 1260 |
| tattcaccaa aaattgtcga taataaggca actgtgacga ttaatatcgc taatcattca | 1320 |
| aatacttcag ataaatataa tgtccatgtt tatacagact acactgatgg gacacattct | 1380 |
| ggtactattt tagggggctta tcagatcaat aaaccgcttg agaaaaatac tgtttcagcc | 1440 |

-continued

```
gatttaacta gtgatggtat tgctctcaaa ttagattcaa acacggttac agattatacc  1500
aaagtacgat ttgccgtttg gtcggatcaa aatggtcaag atgatctcaa gtggtatagt  1560
gcaaatagtg atggaacggc aactgcagct tacagtaacc acagtggtta tgggctttat  1620
catatccata cttatattat taaagatggg aaaatggttg ggcttaatgg caaaacgata  1680
actattaatc agcctagtgc caaggttgat attgctaaag aatccgatgc tctttataaa  1740
gtgactgttt ctaacctgcc agcttacatt agttcagtag ttattcctgt ctggacagat  1800
aaaaacaatc aagatgatat tcaatggatt cccgcgacaa aacaaggtga tggaacctac  1860
gcagcgcaaa ttcagttagc tgatcataat ggggaaacag gccattataa tgttcatgtc  1920
tatggacaaa gtaaatttga caataaagcg gttggtttag cagcaactga tggctttaat  1980
gttgcagaga caaggaatgc tgttatcgct gcttcaaatt ataatgccag tgcaggaacg  2040
atagatatga ttgttaaaca agaagcgggt ggtaaagcca tcaaagaagt tcggatagct  2100
gcttggtcag aagctgatca atctaacctt cattggtatg tttcatcaac tattattgat  2160
ggtaaggtaa cagtcaccat taatgaaaaa aatcatcaat atattaaagg aaattataac  2220
attcatgtct atgttgatta tactgatggc actagtagcg gaaccaatat tggaaactat  2280
agcttgaatg ctgataaacc tgctgttgct ctaccatctt actttattga tattagtagc  2340
cacaatggaa tcatttctgt tgccgaattc aatagcttga aacaacaagg tattcaagga  2400
gtggttgtta agtaacaga aggtacaagc tacatcaatc catatgcaag ttctcaaatt  2460
gccaatgcca gagctgccgg tattaaggtt tctgcttacc attatgctca ctatacttct  2520
gcggccgggg cacaagaaga agcccgttat tttgctaatg cagccagatc ctttggtttg  2580
gaggcatcaa ctgtcatggt caatgatatg gaagaatcct ctatggtgaa caatattaat  2640
aataatgttc aagcttggca agatgagatg aggcgtcaag gttatagcaa cctgattcat  2700
tatactatgg ctagttggtt ggatatacgc ggtgggcaag tagacactgc aaggtttggc  2760
atcaataatt tttgggttgc tcattatgcc aaagggtata cttatatgac tcaagaagaa  2820
gctaaatccc ttaattatta tgctaatgca gcagcttggc agtatactag tgtatcgtct  2880
aaattgtctc atgctttgga tgaaaatatt gattatactg gtcgatttac tcaacagtaa  2940
```

BACTERICIDE HAVING SELECTIVITY TO CARIOGENIC BACTERIUM, AND A METHOD FOR STERILIZATION OF CARIOGENIC BACTERIUM

This application is a National Phase application of PCT/JP2006/314671, filed on Jul. 25, 2006, which claims priority to JP-2006-198407, filed Jul. 20, 2006, and JP 2005-216099, filed Jul. 26, 2005.

FIELD OF THE INVENTION

The present invention relates to a bactericide comprising a bacterial cell wall lytic enzyme having selectivity to a cariogenic bacterium and a surfactant as its effective ingredients. Moreover, the present invention relates to a method for sterilization of a cariogenic bacterium using a bactericide comprising a bacterial cell wall lytic enzyme having selectivity to the cariogenic bacterium and a surfactant as its effective ingredients.

RELATED ART

As the examples of bacteria that cause human dental caries and periodontal disease, two kinds of bacterium, i.e. *Streptococcus mutans* and *Streptococcus sobrinus* (hererafter, refereed to as cariogenic bacterium) are known (Nippon Saikingaku Zassi, 51 (4): 931-951, 1996). Meanwhile, despite of high disease rate of dental caries and periodontal disease, a fundamental therapeutic/prophylactic method for the disease have not been established yet. Recently, xylitol has been attracted attention for its prophylactic effect to dental caries. However, it has only bacteriostatic effect, and can not be used as an aggressive prophylactic agent or a therapeutic agent.

On the other hand, approaches through antibiotic chemical treatment have been made, and numerous antibacterial agents having potent anti-microbial activity and broad antibiotic spectrum have been developed so far. However, such chemotherapeutic antibacterial agents have effects on bacterial groups that form oral bacterial flora, not only bacterium that is the target of chemotherapy, and it causes substituted microbism. Moreover, occurrence of bacterium strains resistant to chemotherapeutic agent has become a serious social problem. Therefore, in order to avoid such problem, application of antibacterial agents having high specificity and effective to only a particular kind of bacterium has been demanded.

To obtain a bactericide that does not cause the problems described above, the present inventors made extensive investigation to find automutanolysin (hereafter, referred to as Aml), which is a bacterial cell wall lytic enzyme specific to cariogenic bacterium (Nippon Saikingaku Zassi, 60 (1): 115, 2005, Japanese Patent Publication No. 2003-419123). For Aml is highly specific toward cariogenic bacterium, it is expected that Aml might be effective for prophylaxis and treatment of dental caries and periodontal disease.

DISCLOSURE OF THE INVENTION

Problem to be Solved by the Invention

However, concerning Aml described above, it has a problem that lysis of cariogenic bacterium by Aml alone takes so long as about 1.5 hour (half-life). The oral cavity is always washed by circulating saliva, therefore, it is difficult to retain Aml at the administrated site for a long period. Then the problem to be solved by the present invention is to increase the action of Aml and to provide a means to shorten the time required for the lysis of cariogenic bacterium within 30 minutes, thereby improving the practical utility of Aml as a bactericide.

The Means to Solve the Problem

To solve the problem described above, the present invention provides a bactericide comprising a bacterial cell wall lytic enzyme having selectivity to a cariogenic bacterium and a surfactant as its effective ingredients. To perform the present invention, said cell wall lytic enzyme having selectivity to the cariogenic bacterium may preferably be Aml. Moreover, said surfactant may preferably be a non-ionic surfactant. Furthermore, said non-ionic surfactant may preferably be a sugar ester, and said sugar ester may preferably be saccharose stearate ester with a HLB value of 15 or 16 or saccharose palmitate ester with a HLB value of 16. Furthermore, a dental caries prophylactic agent, a dental caries therapeutic agent, a dentifrice, a mouthwash or a dental caries prophylactic gum and food containing said bactericide as its effective ingredient are also within the range of this invention.

Moreover, the present invention provides a method for sterilizing a cariogenic bacterium using a bactericide comprising a bacterial cell wall lytic enzyme having selectivity to the cariogenic bacterium and a surfactant as its effective ingredients. To perform the present invention, said bacterial cell wall lytic enzyme having selectivity to cariogenic bacterium may preferably be Aml. Moreover, said surfactant may preferably be non-ionic surfactant. Furthermore, said surfactant may preferably be a sugar ester, said sugar ester may preferably be saccharose stearate ester with a HLB value of 15 or 16 or saccharose palmitate ester with a HLB value of 16.

It was revealed that the action of a bacterial cell wall lytic enzyme to be increased by combining the enzyme with a particular kind of surfactant. By such increased action, the time required for lysis of a cariogenic bacterium by the enzyme can be shortened, and the practical utility of the bacterial cell wall lytic enzyme such as Aml can be improved.

BEST MODE TO CARRY OUT THE INVENTION

Figure 1:
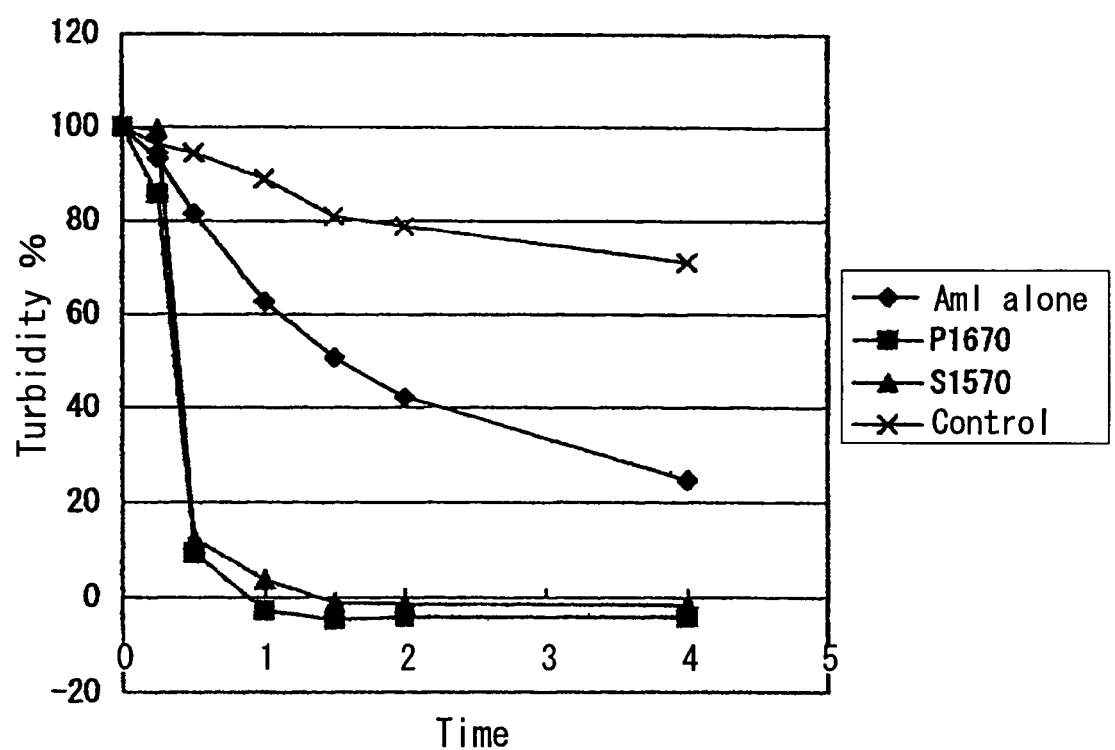
FIG. 1 is a graph comparing the effect of bacteriolysis between an experimental system of Aml alone and an experimental system of Aml added with P1670 and P1570.

As described above, the present invention provides a means to increase the action of a bacterial cell wall lytic enzyme having selectivity to a cariogenic bacterium, by the addition of a particular surfactant to the enzyme such as Aml. Here, Aml referred in this specification means a bacterial cell wall lytic enzyme disclosed in Japanese Patent Publication No. 2003-419123 and in Journal of Japanese Society for Bacteriology, 60 (1): 115, 2005. The Aml is an enzyme from *Streptococcus mutans*, which lyses and sterilizes the pathogenic bacterium itself (*mutans* strain). In addition, Aml is highly specific to the bacterial species and does not affect to other bacterium. Therefore, it is suited to be used for prophylactic or therapeutic agent for dental caries. However, in the present invention, bacterial cell wall lytic enzymes other than Aml can be also used in the present invention.

Meanwhile, Aml referred in this specification means a bactericide comprising a protein according to any one of (1) to (3) described below, which is directed to *Streptococcus mutans* and *Streptococcus sobrinus*. As well, the sequence of Aml is registered to NCBI database as AAN58422.1.

(1) A protein comprising an amino acid sequence represented by SEQ. ID No.1 of a sequence listing, or an amino acid in which a part of the amino acid sequence is deleted, substituted or added and having lytic property to *Streptococcus mutans* and *Streptococcus sobrinus*.

(2) A protein representing a lysis band at 100±10 kDa by zymography using a gel containing killed bacterial bodies of *Streptococcus mutans*.

(3) A protein obtained from a cell, a bacterium, an insect, an animal transformed by a DNA comprising a nucleotide sequence represented by SEQ. ID. No.2 of a sequence listing, or a DNA encoding the protein of (1).

As the surfactant to be added to the bacterial cell wall lytic enzyme having selectivity to the cariogenic bacterium (such as Aml described above), various surfactants can be used. In the present invention, said surfactant may preferably be a non-ionic surfactant, in particular it may preferably be a non-ionic surfactants of a sugar ester, it may further preferably be saccharose stearate ester with a HLB value of 15 or 16 or saccharose palmitate ester with a HLB value of 16.

As the concrete examples of the particularly preferred sugar ester, Ryoto sugar ester S-1570 (Mitsubishi Foods Co. Ltd.), S-1670 (Mitsubishi Foods Co. Ltd.) and P-1670 (Mitsubishi Foods Co. Ltd.) can be listed. However, the sugar ester applicable to this invention is not limited to them.

The Ryoto sugar ester S-1570 is a saccharose stearate ester with a HLB value of 15 as its physical property, which contains about 70% of stearic acid as the bonded fatty acid and an ester composition consisting of about 70% of monoester and about 30% of di-, tri-, polyester. Moreover, the Ryoto sugar ester S-1670 is also a saccharose stearate ester with a HLB value of 16 as its physical property, which contains about 70% of stearic acid as the bonded fatty acid and an ester composition consisting of about 75% of monoester and about 25% of di-, tri-, polyester.

Furthermore, the Ryoto sugar ester P-1670 is a saccharose palmitate ester with a HLB value of 16 as its physical property, which contains about 80% of palmitic acid as the bonded fatty acid and an ester composition consisting of about 80% of monoester and about 20% of di-, tri-, polyester.

The concentration of Ryoto sugar ester S-1570, S-1670 and P-1670 to be utilized in this invention is not particular limited, so long as having the effect to increase the lytic activity of Aml. However, the surfactants may preferably be utilized at the concentration of not lower than 0.001%, more preferably be utilized at the concentration of not lower than 0.025%, further more preferably be utilized at the concentration of not lower than 0.05%. Despite of it, the concentration of the surfactant to be utilized is not limited with the range described above.

Meanwhile, in Japanese Patent Publication 9-322763, it is described that a lytic enzyme exhibiting lytic activity to the cell wall of *Aureobasidium pullulans* can be combined with a surfactant such as amphorex LB-2 to increase the lytic effect of the enzyme. However, *Aureobasidium pullulans* utilized in Japanese Patent Publication 9-322763 is not a cariogenic bacterium, therefore, the description of Japanese Patent Publication 9-322763 does not provide a utility in the field of dentistry. Moreover, the lytic enzyme used in Japanese Patent Publication 9-322763 is quite different from the Aml.

The bactericide according to this invention can be used for various utilities. As the concrete examples of the practical utilities, a dental caries prophylactic agent, a tooth cavity therapeutic agent, a dentifrice, a mouthwash, a dental caries prophylactic gum and food can be listed, however, the utility of the bactericide according to the present invention is not limited to them. As well, a dental caries prophylactic agent, a tooth cavity therapeutic agent, a dentifrice, a mouthwash, a dental caries prophylactic gum and food containing the bactericide according to the present invention can be manufactured using the techniques well-known to the skilled artisan.

The present invention will be explained in detail according to the Example in the following, the range of the present invention is not limited to them.

EXAMPLE 1

The method for measuring the bacteriolytic effect adopted in the present invention is as follows.

The bacterial strain to be measured its bacteriolytic effect was cultivated overnight, it was washed by physiological saline then suspended into 0.1M phosphate buffer (pH 6.8) containing 0.1M NaCl and 0.1 mM $CaCl_2$. The cell body was treated by ultrasonic generator to disperse the cell body. Thereafter, 500 μg/ml Aml solution dissolved into 30% ethyleneglycol-0.1M sodium phosphate buffer (pH 6.3) and 5 mg/ml surfactant dissolved into distilled water (40 μl) were added into a system consisting of 1 ml of bacterial suspension. 0.1M phosphate buffer solution and 0.1 mM calcium. It was incubated at 37° C., then the turbidity was measured with time, and the bacteriolytic effect was evaluated using the rate of decrease in turbidity as an index.

Using *Streptcoccus mutans* 403R (dental caries causing bacterium), the bacteriolytic effect was measured with time using an experimental system of Aml alone, and an experimental system of Aml added with P1670 or S1570 at the concentration of 0.05% (Table 1, FIG. 1). In table 1 and FIG. 1, the turbidity of the bacterial solution at the beginning of the experiment was indicated as 100%, and the bacteriolytic effect was represented by the percentage of turbidity at each time point. As shown from FIG. 1, in the group added with surfactant P1670 and surfactant S1570, it was recognized that the bacteriolytic effects of the groups were apparently stronger compared with the system of Aml alone. Moreover, in the systems of Aml added with 0.05% of P1670 or S1570, the time required for bacteriolysis of 50% of bacteria (ED50) was about 30 minutes. By the way, the control indicates a system in which only a cariogenic bacterium was cultivated.

TABLE 1

| Time | Aml alone | P1670 | S1570 | Control |
|---|---|---|---|---|
| 0 | 100.0 | 100.0 | 100.0 | 100.0 |
| 0.25 | 93.3 | 85.7 | 99.4 | 96.3 |
| 0.5 | 81.5 | 9.2 | 12.2 | 94.5 |
| 1 | 62.6 | −2.8 | 3.7 | 88.9 |
| 1.5 | 50.8 | −4.8 | −1.1 | 80.9 |
| 2 | 42.2 | −4.2 | −1.4 | 78.8 |
| 4 | 24.6 | −4.2 | −1.7 | 71.1 |

Figure 2:
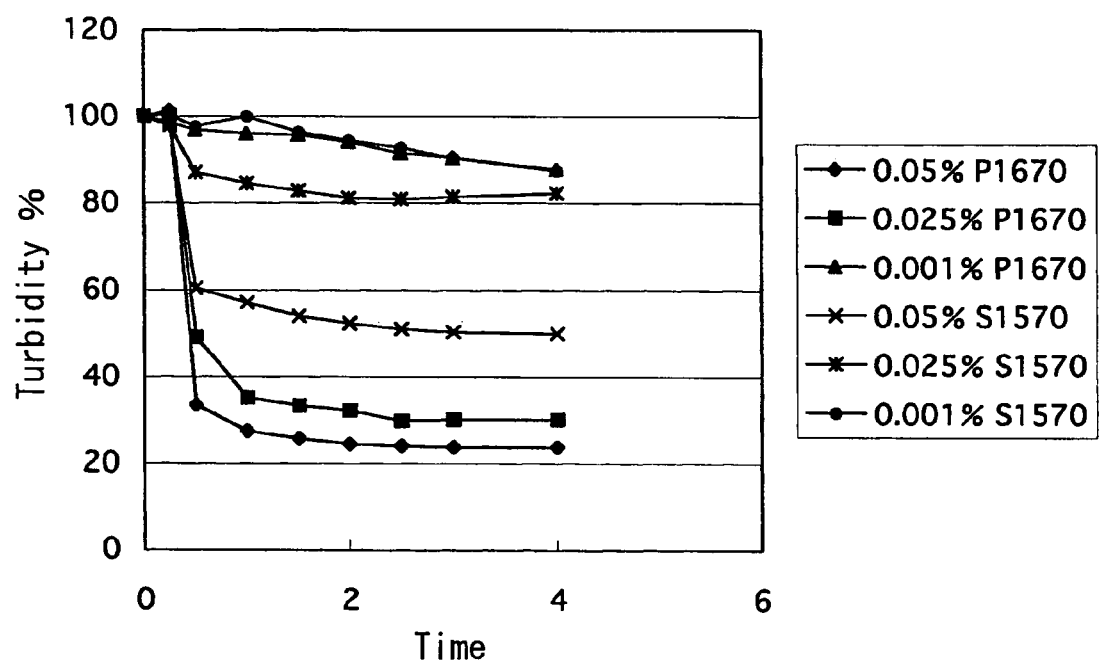
FIG. 2 is a graph showing dose-dependency of surfactants toward bacteriolytic effect in an experimental system of Aml combined with the surfactants (P1670 or S1570).

Using *Streptcoccus mutans* 403R, the bacteriolytic effect was measured with time on systems in which P1670 or S1570 was added into Aml at various final concentrations (0.05%, 0.025%, 0.001%) (Table 2, FIG. 2). As shown in Table 2 and FIG. 2, the bacteriolytic effect was observed dose-dependent manner on both groups added with P1670 or S1570. That is, significant bacteriolytic effect was not recognized on P1670 and S1570 at the surfactant concentration of 0.001%. On the other hand, significant bacteriolytic effect was recognized on P1670 at the surfactant concentration of 0.05% and 0.025%, and on S1570 at the surfactant concentration of 0.05%.

TABLE 2

| Time | 0.05% P1670 | 0.025% P1670 | 0.001% P1670 | 0.05% S1570 | 0.025% S1570 | 0.001% S1570 |
|---|---|---|---|---|---|---|
| 0 | 100.0 | 100.0 | 100.0 | 100.0 | 100.0 | 100.0 |
| 0.25 | 101.3 | 100.3 | 98.6 | 98.3 | 97.8 | 100.3 |
| 0.5 | 33.4 | 49.1 | 96.9 | 60.3 | 87.2 | 97.7 |
| 1 | 27.3 | 35.1 | 96.0 | 57.0 | 84.6 | 100.0 |
| 1.5 | 25.6 | 33.3 | 95.8 | 54.0 | 83.0 | 96.4 |
| 2 | 24.4 | 32.2 | 94.1 | 52.3 | 81.3 | 94.4 |
| 2.5 | 24.0 | 29.9 | 91.5 | 51.0 | 81.0 | 92.8 |
| 3 | 23.7 | 30.2 | 90.4 | 50.3 | 81.6 | 90.5 |
| 4 | 23.7 | 30.2 | 87.9 | 50.0 | 82.4 | 87.5 |

Figure 3:
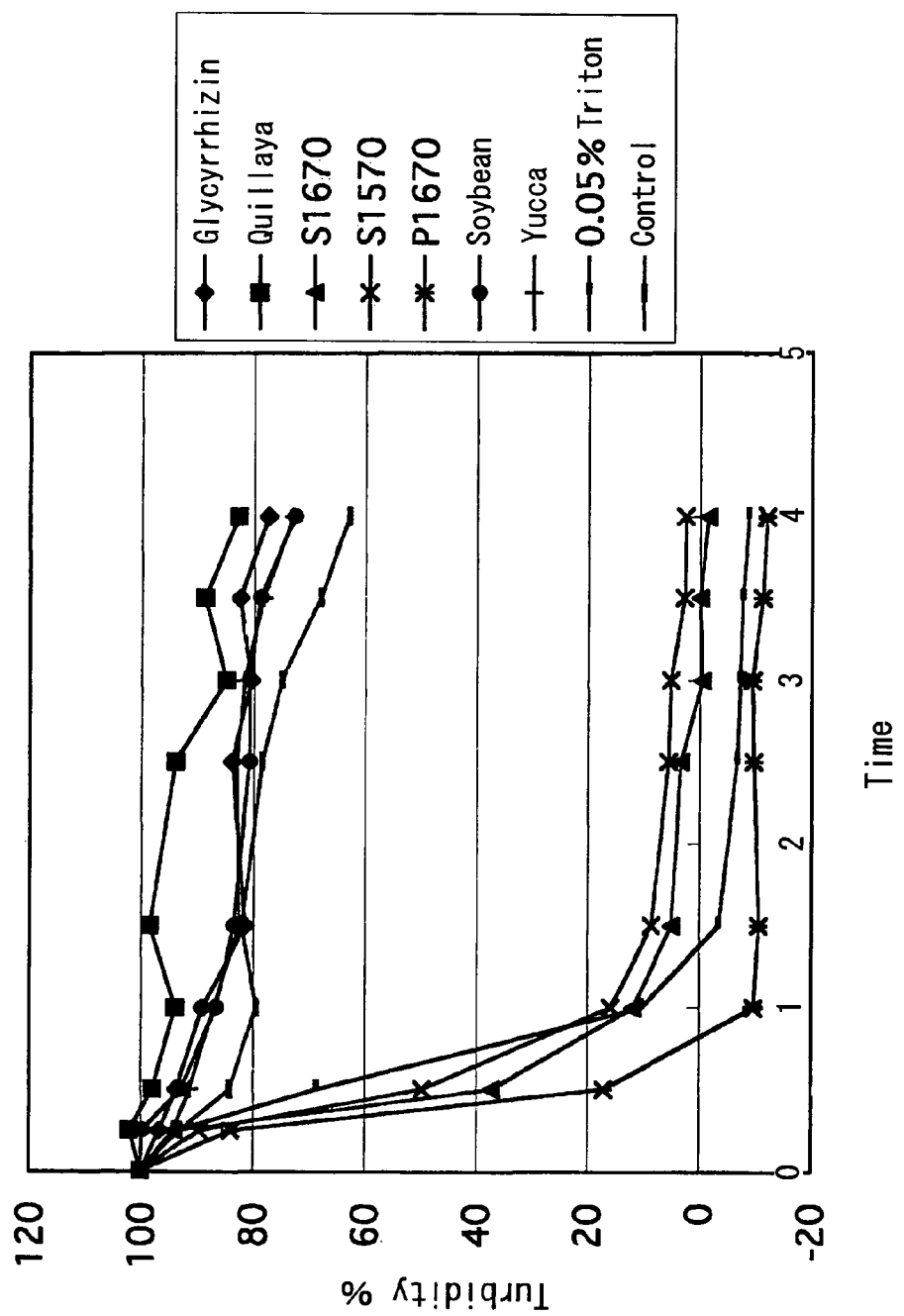
FIG. 3 is a graph showing the effect of bacteriolysis investigated on experimental systems of Aml added with various surfactants.

Using *S. mutans* PMZ175 (a cariogenic bacterium), the bacteriolytic effect was investigated using experimental systems in which various surfactants were added to Aml (FIG. 3, Table 3). Meanwhile, the food additives investigated in this experiment were glycyrrhizin (0.5%), saponin from quillaya (0.5%), S1670 (0.1%), S1570 (0.05%), P1670 (0.05%), saponin from soybean (0.05%), saponin from yucca (0.05%), and Triton X (0.05%). Among various surfactants investigated in Table 3 and FIG. 3, a bacteriolytic effect equal or more potent compared with TritonX was recognized for only S1670, S1570, P1670 by combining with Aml, and no bacteriolytic effect was recognized in the systems where other surfactants were added.

TABLE 3

| Time | 0.5% Glycyrrhizin | 0.5% Quillaya | 0.1% S1670 | 0.05% S1570 | 0.05% P1670 | 0.05% Soybean | 0.05% *Yucca* | 0.05% Triton | Control |
|---|---|---|---|---|---|---|---|---|---|
| 0 | 100.0 | 100.0 | 100.0 | 100.0 | 100.0 | 100.0 | 100.0 | 100.0 | 100.0 |
| 0.25 | 96.6 | 102.1 | 94.0 | 89.6 | 83.8 | 99.6 | 94.1 | 93.8 | 93.0 |
| 0.5 | 93.6 | 97.8 | 37.2 | 49.6 | 17.0 | 92.8 | 91.2 | 68.6 | 84.1 |
| 1 | 89.0 | 93.9 | 11.8 | 15.8 | −9.7 | 86.6 | 87.0 | 10.3 | 79.4 |
| 1.5 | 81.3 | 98.4 | 4.9 | 8.5 | −10.0 | 83.5 | 82.5 | −3.4 | 81.9 |
| 2.5 | 83.7 | 93.9 | 3.3 | 5.4 | −9.7 | 80.7 | 82.9 | −6.6 | 78.4 |
| 3 | 80.3 | 84.8 | −0.5 | 5.1 | −9.5 | 80.7 | 81.6 | −7.1 | 75.0 |
| 3.5 | 82.3 | 88.7 | 0.0 | 2.7 | −11.2 | 78.8 | 78.3 | −7.7 | 68.0 |
| 4 | 77.4 | 82.7 | −1.5 | 2.4 | −12.0 | 72.6 | 72.9 | −8.8 | 62.9 |

Figure 4:
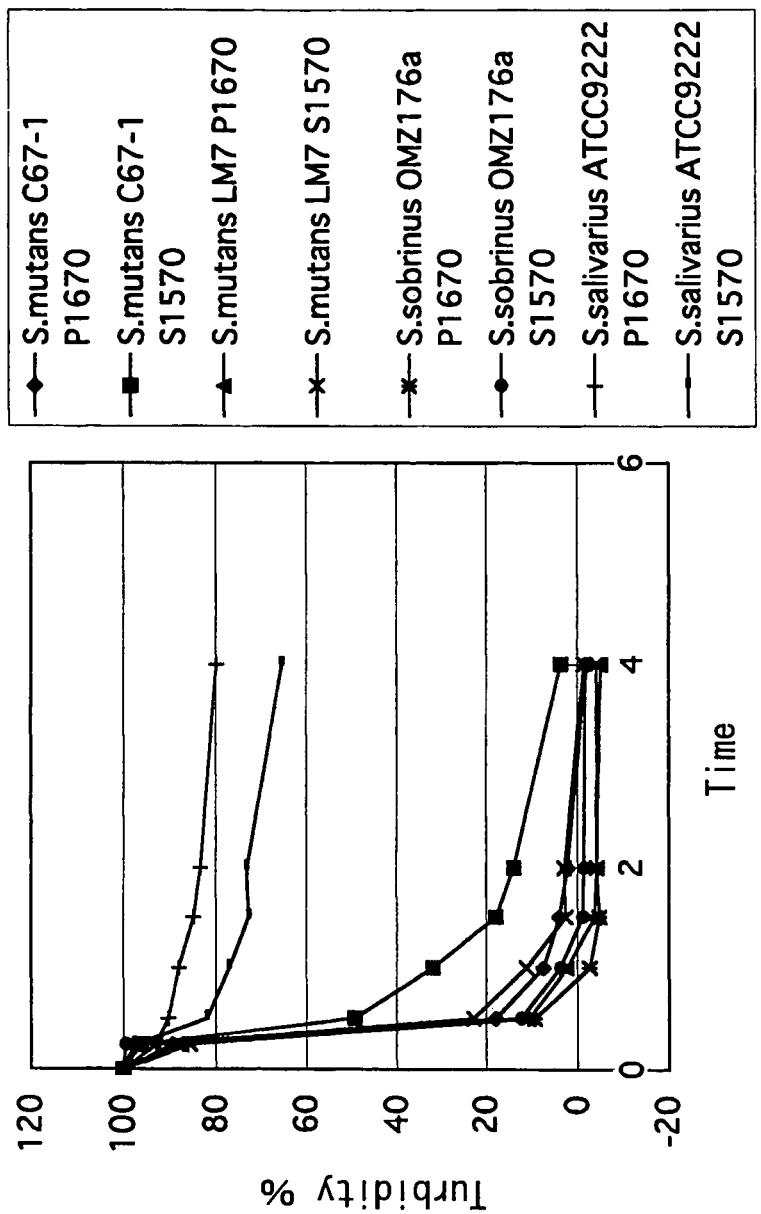
FIG. 4 is a graph showing the effect of bacteriolysis investigated on various oral bacteria.

Furthermore, by investigating bacteriolytic effects using various oral bacterium strains, it was investigated whether the bacteriolytic effect is specific to cariogenic bacteria or not. The bacterium strains utilized in this experiment were *Streptococcus mutans* C67-1, *Streptococcus mutans* LM7, *Streptococcus sobrinus* OMZ176a which are cariogenic bacteria, and *Streptococcus salivarius* ATCC9222 which is not a cariogenic bacterium. Using these bacterium strains, Aml was combined with 0.05% of P1670 or S1570, and the bacteriolytic effect was investigated on the respective strains (Table 4, FIG. 4). As a result, concerning *Streptococcus salivarius* ATCC9222, synergistic effect on bacteriolysis was not recognized when Aml was combined with P1670 or S1570. On the other hand, concerning cariogenic bacterium, synergistic effect on bacteriolysis was recognized when Aml was combined with P1670 or S1570. Therefore, it was admitted that the bacteriolytic effect was specific for *Streptococcus mutans* (C67-1, LM7) and *Streptococcus sobrinus* (OMZ176a), which are cariogenic bacteria.

TABLE 4

| Time | *S. mutans* C67-1 | | *S. mutans* LM7 | | *S. sobrinus* OMZ176a | | *S. salivarius* ATCC9222 | |
| --- | --- | --- | --- | --- | --- | --- | --- | --- |
| | P1670 | S1570 | P1670 | S1570 | P1670 | S1570 | P1670 | S1570 |
| 0 | 100.0 | 100.0 | 100.0 | 100.0 | 100.0 | 100.0 | 100.0 | 100.0 |
| 0.25 | 89.5 | 96.4 | 87.5 | 93.3 | 85.7 | 99.4 | 93.1 | 97.7 |
| 0.5 | 17.9 | 49.3 | 10.5 | 22.7 | 9.2 | 12.2 | 90.3 | 81.9 |
| 1 | 7.4 | 31.8 | 2.3 | 11.0 | −2.8 | 3.7 | 88.1 | 77.0 |
| 1.5 | 3.9 | 17.9 | −3.7 | 2.5 | −4.8 | −1.1 | 84.9 | 72.8 |
| 2 | 2.1 | 13.9 | −4.3 | 2.8 | −4.2 | −1.4 | 83.4 | 73.2 |
| 4 | −2.1 | 3.6 | −5.1 | −1.4 | −4.2 | −1.7 | 79.9 | 65.4 |

From the results described above, by combining Aml with surfactants (Ryoto sugar ester S-1570, S-1670, P-1670), bacteriolytic effect of Aml, which is dependent on the concentration of the surfactants, was recognized. Moreover, the time required for the bacteriolysis of 50% of living bacterium (ED50) was about 30 minutes, therefore, the time required for the bacteriolysis was shortened significantly, when compared with 1.5 hour in the case of Aml alone. Furthermore, the bacteriolytic effect obtained by combining Aml with the surfactant was specific to cariogenic bacterium.

INDUSTRIAL APPLICABILITY

According to the present invention, the bacteriolytic effect of a bacterial cell wall lytic enzyme can be increased by the addition of a surfactant to the enzyme. As a result, the time required for lysis of cariogenic bacterium with bacterial cell wall lytic enzyme can be shortened, and the practical utility of the bacterial cell wall lytic enzyme at the field of dentistry can be improved. The bactericide according to the present invention, comprising a bacterial cell wall lytic enzyme and a surfactant as its effective ingredients can be applied for various uses, such as a dental caries prophylactic agent, a dental caries therapeutic agent, a dentifrice, a mouthwash, or a dental caries prophylactic gum and food.

The invention claimed is:

1. A bactericide comprising:
a bacterial cell wall lytic enzyme having selectivity to a cariogenic bacterium; and
a surfactant,
wherein:
the cell wall lytic enzyme is automutanolysin,
the automutanolysin comprises the full-length amino acid sequence of SEQ ID NO: 1,
the cariogenic bacterium is *Streptococcus mutans* or *Streptococcus sobrinus*,
the surfactant is saccharose stearate ester or saccharose palmitate ester, and is present in the bactericide at a concentration of not lower than 0.025%,
the saccharose stearate ester has an HLB value of 15 and comprises:
about 70% of stearic acid as a bonded fatty acid, and
an ester composition consisting of about 70% of monoester and about 30% of di-, tri-, and/or polyester, and
the saccharose palmitate ester has an HLB value of 16 and comprises:
about 80% of palmitic acid as a bonded fatty acid, and
an ester composition consisting of about 80% of monoester and about 20% of di-, tri-, and/or polyester.

2. A dental caries prophylactic agent, a dental caries therapeutic agent, a dentifrice, a mouthwash, or a dental caries prophylactic gum and food comprising the bactericide according to claim 1 as its effective ingredient.

3. A method for sterilization of a cariogenic bacterium using a bactericide comprising a bacterial cell wall lytic enzyme having selectivity to the cariogenic bacterium and a surfactant, wherein:
the cariogenic bacterium is *Streptococcus mutans* or *Streptococcus sobrinus*,
the bacterial cell wall lytic enzyme is automutanolysin,
the automutanolysin comprises the full-length amino acid sequence of SEQ ID NO: 1,
the surfactant is saccharose stearate ester or saccharose palmitate ester and is present in the bactericide at a concentration of not lower than 0.025%,
the saccharose stearate ester has an HLB value of 15 and comprises:

about 70% of stearic acid as a bonded fatty acid, and
an ester composition consisting of about 70% of monoester and about 30% of di-, tri-, and polyester. and the saccharose palmitate ester has an HLB value of 16 and comprises:
about 80% of palmitic acid as a bonded fatty acid, and
an ester composition consisting of about 80% of monoester and about 20% of di-, tri-, and polyester.

4. The bactericide according to claim 1, wherein the surfactant is P1670 or S1570.

* * * * *